United States Patent [19]

Gottesman et al.

[11] Patent Number: 5,229,273

[45] Date of Patent: Jul. 20, 1993

[54] PURIFIED BACTERIAL PROTEIN WHICH STIMULATES LIGATION OF NUCLEIC ACID MOLECULES

[75] Inventors: Max Gottesman; William Holloman, both of New York, N.Y.

[73] Assignee: The Trustees of Columbia University in the City of New York, New York, N.Y.

[21] Appl. No.: 530,922

[22] Filed: May 30, 1990

[51] Int. Cl.[5] .................. C12N 15/33; C12N 15/52; C12N 15/70; C12N 9/00

[52] U.S. Cl. ........................ 435/69.1; 435/71.2; 435/183; 435/252.33; 435/320.1

[58] Field of Search .............. 530/350, 825; 536/27; 435/69.1, 71.2, 320.1, 252.33, 183

[56] References Cited

PUBLICATIONS

B. E. Windle et al., *Proc. Natl. Acad. Sci. USA* 83:3885-3889, Jun. 1986.

B. E. Windle et al., *J. of Bacteriology* 170:4881-4889, Oct. 1988.

S. D. Lu et al., *J. of Bacteriology* 171:3427-3442, Jun. 1989.

*Primary Examiner*—Robert A. Wax
*Assistant Examiner*—Stephen Walsh
*Attorney, Agent, or Firm*—John P. White

[57] ABSTRACT

The subject invention provides a purified protein having a molecular weight of about 22.8 kDa and the amino acid sequence shown in FIG. 2. The invention further provides a method of producing the 22.8 kDa protein which comprises culturing the host cell comprising an expression vector under conditions such that the expression vector contained therein expresses the protein and recovering from the host cell the protein so expressed. Also provided is a method of ligating separate nucleic acid molecules which comprises contacting the molecules with the 22.8 kDa protein under conditions such that the molecules are ligated together.

3 Claims, 4 Drawing Sheets

Figure 2

```
197    AACTACGAAG ACGTTGCCAT TACTTCACTC CTTGACATCA TTGGCGGCCA

247    TTAGGCCGCC TTTTTTTTGC CATATGAAAA CAATCGAACA AAAAATTGAA
                                  M  K  T  I  E  Q  K  I  E

297    CAGTGCCGCA AGTGGCAGAA GGCAGCCAGA GAACGAGCGA TCGCTCGGCA
        Q  C  R  K  W  Q  K  A  A  R  E  R  A  I  A  R  Q

347    ACGGGAGAAG TTGGCTGATC CGGTCTGGCG AGAATCTCAA TATCAGAAAA
        R  E  K  L  A  D  P  V  W  R  E  S  Q  Y  Q  K  M

397    TGCGGGATAC TCTCGACCGC CGTATCGCTA AACAGAAAGA GCGCCCACCA
        R  D  T  L  D  R  R  I  A  K  Q  K  E  R  P  P

447    GCCAGCAAAA CGCGGAAAAG CGCGGTAAAA ATAAAATCTC GTGGCTTGAA
        A  S  K  T  R  K  S  A  V  K  I  K  S  R  G  L  K

497    GGGGAGAACA CCAACGGCGG AGGAACGGCG CATCGCCAAT GCTCTTGGCG
        G  R  T  P  T  A  E  E  R  R  I  A  N  A  L  G  A

547    CTCTCCCCTG CATTGCCTGC TATATGCATG GAGTAATATC TAATGAGGTG
        L  P  C  I  A  C  Y  M  H  G  V  I  S  N  E  V

597    TCTCTGCACC ATATCGCCGG TCGTACCGCG CCGGGTTGTC ATAAAAAGCA
        S  L  H  H  I  A  G  R  T  A  P  G  C  H  K  K  Q

647    ATTGCCACTT TGTAGATGGC ACCACCAGCA TGCAGCTCCG GCTGAAGTAA
        L  P  L  C  R  W  H  H  Q  H  A  A  P  A  E  V  R

697    GAGAAAAATA CCCATGGCTG GTCCCTGTTC ATGCCGATGG TGTGGTTGGA
        E  K  Y  P  W  L  V  P  V  H  A  D  G  V  V  G

747    GGCAAGAAAG AATTCACCTT GCTGAACAAG TCAGAGATGG AGTTACTGGC
        G  K  K  E  F  T  L  L  N  K  S  E  M  E  L  L  A

797    TGACGCCTAT GAGATGGCAA ACATCATGCA CTAATAAATA TATTATTTTT
        D  A  Y  E  M  A  N  I  M  H  ---

847    AATGATAAAT GATTGACAAC TGACAAGTGA CTTCAGTCAG AATCATCACA

897    CGCCCGGTAC GGATGGATCC
```

PURIFIED BACTERIAL PROTEIN WHICH STIMULATES LIGATION OF NUCLEIC ACID MOLECULES

The invention described herein was made in the course of work under Public Health Service grant CA23767-10 from the National Institutes of Health. The U.S. Government may have certain rights in this invention.

BACKGROUND OF THE INVENTION

Several temperate coliphages are known to express recombination functions. The int and xis genes of lambda, for example, specify site-specific recombination enzymes, while the reda and redb gene products, λ exonuclease and beta protein, respectively, promote homologous recombination. The four genes are clustered in the lambda genome, and their roles in lambda physiology are known; the first two are required for prophage integration and excision, whereas the products of the red genes convert lambda monomers into packageable multimers.

Prophage P1 expresses a site-specific recombination function, Cre, which improves P1 plasmid maintenance by cutting and rejoining P1 chromosomes at the P1 lox sites (Hochman, L., et al. 1983. Virology 131:11-17; Sternberg, N., et al. 1980. Cold Spring Harbor Symp. Quant. Biol. 45:297-309; Sternberg, N., et al. 1986. J. Mol. Biol. 187:197-212). RecA is responsible for most P1 circularization, since Cre can circularize only those P1 molecules, about 20% of the total, which bear redundant lox sites. In recA mutants, however, Cre is essential for P1 lysogenization and lytic growth.

The lytic development of P1 prophage is blocked by the bacteriophage-encoded cI gene product. Lysogens carrying P1c1.100, a cIts mutant, are stable at 32° C. but are induced at temperatures above 39° C. (Rosner, J. L. 1972. Virology 48:679-689). Several years ago, applicants observed that P1c1.100 lysogens displayed a phenotype related to recombination. Escherichia coli bearing the IS1 gal operon insertion, galTN102 (Jordan, E., et al. 1967. Mol. Gen. Genet. 100:296-306), revert to Gal+ at elevated frequencies when lysogenic for P1cIts. This reversion probably results from recombination between the repeated 9-base-pair (bp) galT target sequences which flank the IS1 transposon, a process referred to as precise excision. Independently, Windle and Hays (Windle, B. E. and J. B. Hays. 1986. Proc. Natl. Acad. Sci. USA 83:3885-3889) noted that recombination between two close but nonoverlapping deletions in lacZ was likewise increased by P1c1.100 prophage. P1c1.100 did not appear to stimulate recombination within large regions of DNA homology (Windle, B. E. and J. B. Hays. 1986. Proc. Natl. Acad. Sci. USA 83:3885-3889). These observations suggested that P1 carries a recombination enhancement function (ref) which specifically stimulates recombination between small segments of homologous DNA flanked by non-homologous sequences.

Little is known about microhomologous recombination. Excision of transposons does not depend upon transposase activity and is at least partially independent of the E. coli RecA pathway. Indeed, RecA does not efficiently promote pairing between homologous DNA segments 30 bp or less in extent (Argus, P., et al. 1986. EMBO J. 5:433-440). Several bacterial functions have been implicated in precise excision; mutations that stimulate the reaction have been mapped to recBC, uvrD, (mutU) mutH, mutL, mutS, mutD, ssb, and dam (Lundblad, V. and N. Kleckner. 1985. Genetics 109:3-19). Mutations in mutU and dam, as well as a variety of mutations which result in the accumulation of DNA replicative fragments, increase micro-homologous recombination in lacZ (Konrad, E. B. 1977. J. Bacteriol. 130:167-172). No demonstration of RecA-independent microhomologous recombination in vitro has been reported.

The subject invention describes the cloning and sequencing of the P1 ref gene and the overproduction of Ref in an expression vector system. Ref stimulation of precise excision is entirely dependent on the RecA pathway. In agreement with previously reported data (Windle, B. E. and J. B. Hays. 1986. Proc. Natl. Acad. Sci. USA 83:3885-3889), Ref does not play an indispensable role in the physiology of phage P1.

Applicants have found that Ref is useful for stimulating ligation of nucleic acid molecules.

SUMMARY OF THE INVENTION

The subject invention provides a purified protein having a molecular weight of about 22.8 kDa and the amino acid sequence shown in FIG. 2. Further provided is a nucleic acid such as DNA having the coding sequence shown in FIG. 2, which encodes the 22.8 kDa protein.

The invention also provides an expression vector such as a plasmid comprising the DNA encoding the 22.8 kDa protein and suitable regulatory elements so positioned with respect to the DNA as to permit expression thereof in a suitable host such as a bacterial cell.

The invention further provides a method of producing the 22.8 kDa protein which comprises culturing the host cell comprising the expression vector or expression plasmid under conditions such that the expression vector or expression plasmid contained therein expresses the protein and recovering from the host cell the protein so expressed.

Also provided is a method of ligating separate nucleic acid molecules which comprises contacting the molecules with the 22.8 kDa protein under conditions such that the molecules are ligated together.

BRIEF DESCRIPTION OF THE FIGURES

FIG. 2. Sequence of the P1 ref gene. The sequence of the 720-bp HincII to BamHI fragment carried by pLSD10 (see FIG. 1) was determined by the Genex Company, Rockville, Md., using the Sanger dideoxy strategy. The numbering of the nucleotides begins at the HpaI site; the sequence between this site and the HincII site has been determined previously (Windle, B. E., et al. 1988. J. Bacteriol. 170:4881–4889).

DETAILED DESCRIPTION OF THE INVENTION

Figure 1:
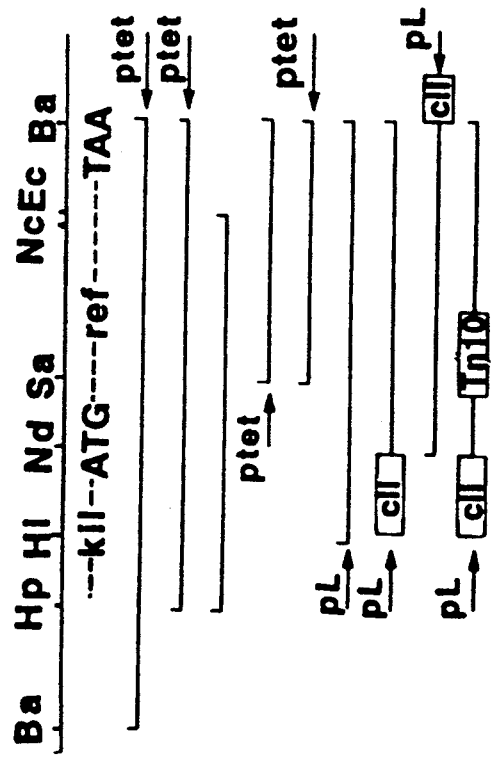
FIG. 1. Construction of ref region plasmids from the P1 BamHI-8 fragment. Constructions are described in detail in Results. P1 cre lies to the left of the BamHI site and is transcribed from left to right. Distances between restriction sites in the BamHI-8 fragment are drawn approximately to scale. The locations of the P1 kil and ref genes are shown. The ptet and $p_L$ promoters of pBR322 and phage λ and the direction of transcription are indicated. Restriction site abbreviations: Ba, BamHI; Hp, HpaI; Hi, HincII; Nd, NdeI; Sa, Sau3A; Nc, NcoI; Ec, EcoRI. The presence of the P1 kil gene on a plasmid is indicated by the inability to transform non-P1 lysogens. Ref activity is estimated by the number of Gal+ red papillae appearing in N6345 and its derivatives, after incubation at 32° C. for 72 h on MacConkey galactose indicator plates. Symbols: −, 1 red papilla per $10^5$ colonies; wk, 1 red papilla per $10^2$ colonies; +, 1 to 10 red papillae on each colony; +++, 10 to 100 red papillae per colony.

The plasmid pLSD13 distributed in *Escherichia coli* strain N7298 was deposited pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession No. 68326.

The subject invention provides a purified protein having a molecular weight of about 22.8 kDa and the amino acid sequence shown in FIG. 2. Also provided is a nucleic acid, such as DNA, encoding the 22.8 kDa protein. The DNA molecule may have the coding sequence shown in FIG. 2.

Also provided is a vector Comprising the DNA molecule encoding the 22.8 kDa protein. Examples of vectors are viruses such as bacteriophages (such as phage lambda), cosmids, plasmids and other recombination vectors. In a preferred embodiment of the invention, the vector is a plasmid. Nucleic acid molecules are inserted into vector genomes by methods well known in the art. For example, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available.

Also provided is an expression vector comprising the DNA molecule encoding the 22.8 kDa protein and suitable regulatory elements, such as promoters, operators and repressors, so positioned with respect to the DNA as to permit expression of the protein in a suitable host. In preferred embodiments of the invention, the regulatory elements are positioned close to and upstream of the DNA encoding the polypeptide.

Further provided is an expression plasmid comprising the DNA molecule encoding the 22.8 kDa protein and suitable regulatory elements so positioned with respect to the DNA as to permit expression of the protein in a suitable host. The regulatory elements are as described above for expression vectors. The plasmid may be constructed by methods well known in the art. A specific example of an expression plasmid is an expression plasmid designated pLSD13, which overproduces the 22.8 kDa protein.

The expression vector of this invention may be introduced into a suitable host cell. The expression plasmid, for example, may be introduced into a bacterial host cell. A suitable bacterial host cell is an *Escherichia coli* cell. In a preferred embodiment of the invention, the *Escherichia coli* cell with the plasmid pLSD13 distributed therein is strain N7298 deposited under ATCC Accession No. 68326. Other *Escherichia coli* strains and other bacteria can also be used as host cells for the plasmids.

The invention also provides a method of producing a purified protein having a molecular weight of about 22.8 kDa and the amino acid sequence shown in FIG. 2. The method comprises culturing the host cell harboring the expression vector comprising the DNA encoding the protein and suitable regulatory elements under conditions such that the expression vector contained therein expresses the protein and recovering from the host cell the protein so expressed.

Also provided is a method of producing a purified protein having a molecular weight of about 22.8 kDa and the amino acid sequence shown in FIG. 2 which comprises culturing the *Escherichia coli* strain N7298 cell under conditions such that the expression plasmid contained therein expresses the protein and recovering from the *Escherichia coli* cell the protein so expressed.

The invention further provides a method of ligating separate nucleic acid molecules. The method comprises contacting the nucleic acid molecules with the 22.8 kDa protein under conditions such that the molecules are ligated together. In a preferred embodiment of the invention, the nucleic acid molecules are double-stranded. In another preferred embodiment of the invention, the nucleic acid molecules are blunt-ended. The nucleic acid molecules to be ligated can also have cohesive ends.

MATERIALS AND METHODS

Plasmids and phage. pKC30 is a pBR322-derived $\lambda$ $p_L$ expression vector (Maniatis, T., et al. 1982. Molecular Cloning: A Laboratory Manual. Cold Spring Harbor Laboratory, Cold Spring Harbor, N.Y.; Rao, R. N. 1984. Gene 31:247–250). $\lambda$D69 is a $\lambda$ imm$^{21}$ cloning vector (Mizusawa, S. and D. F. Ward. 1982. Gene 20:317–322). plasmid pNK1340 was kindly provided by N. Kleckner. It donates a mini-Tn10 of approximately 2.9 kilobases (kb). The mini-Tn10, once transferred, is stable, since the IS10 transposase gene is not included in the transposon.

p124 is a gal+ pBR322 clone isolated by A. Majumdar. The plasmids (FIG. 1) were constructed as follows, using standard recombinant DNA techniques (Maniatis, T., et al. 1982. Molecular Cloning: A Laboratory Manual. Cold Spring Harbor Laboratory, Cold Spring Harbor, N.Y.). pLD3 carries the P1 BamHI-8 fragment (ca. 1.8 kb) in the BamHI site of pBR322 with ref in the antisense orientation relative to that of tet. pLSD1 was obtained by digestion of pLD3 with PvuII and HpaI and religation; the former cleaves in pBR322, and the latter cleaves within the p1 DNA fragment. pLSD4 was derived from pLSD1 by cutting at the plasmid and ref EcoRI sites and religating. pLSD16 and pLSD17 carry the 553-bp Sau3A P1 DNA fragment cloned into the BamHI site of pBR322 in opposite orientations; in pLSD16, the ref sense strand is transcribed from ptet. pLSD10 was constructed by inserting the 720-bp HincII-BamHI P1 DNA fragment from pLSD1 into the large HpaI-BamHI fragment from pKC30. pLSD10 is a $p_L$-N'-ref-tet transcription fusion; it is $Amp^r$ and $Tet^s$ and carries the mutant N gene. pLSD14 was constructed from NdeI-digested pLSD10 and pOG7. pOG7 is a $p_L$ expression vector carrying the ribosome-binding site and ATG of the λ cII gene (Oppenheim, A. B., et al. 1982. J. Mol. Biol. 158:327–346). The 650-bp P1 DNA fragment of the former was inserted into the large fragment of pOG7. The orientation of ref with respect to $p_L$ in pLSD14 is antisense. Accordingly, applicants digested pLSD14 with NdeI, religated, and obtained pLSD13, which carries a cII-ref translation fusion: $p_L$-nutL-N"cro-nutR-tR1-RBS$^{cII}$-ATG ... ref ... TAA-.

pLSD15, carrying a ref::mini-Tn10 mutation, was obtained by homologous recombination between pLSD13 and λ ref::Tn10 as described below.

P1 and λ stocks were prepared by standard protocols, as was phage and plasmid DNA (Silhavy, T. J., et al. 1984. Experiments with Gene Fusions. Cold Spring Harbor Laboratory, Cold Spring Harbor, N.Y.). λ lysogens were prepared as previously described (Gottesman, M. E. and M. B. Yarmolinsky. 1968. J. Mol. Biol. 31:487–505). All P1 carry the Tn9 $Cm^r$ marker. P1 $Cm^r$ and P7 $Ap^r$ lysogens were selected from among infected cells by the appropriate antibiotic resistance.

Bacterial strains. N6405 is C600 $r_k^-m_k^+$ for λ c1857 $N^+$. It derives from N4830 (Gottesman, M. E., et al. 1980. J. Mol. Biol. 140:57–75). The prophage carries two deletions: (i) delBam, which removes DNA between λ coordinates 27973 and 34500, and (ii) delH1, which removes prophage genes from cro through attR. N6345 is W3110 $F^-$ his ilv galTN102.

Analysis of chromosomal gal DNA. A galTn102 derivative of plasmid pI24 was isolated by extracting plasmid DNA from N6345(pI24), transforming a gal deletion strain (RW1401), and selected $Gal^-$ colonies. These colonies appear at a frequency of ca. $10^{-4}$ and carry pI24 galTN102; the IS1 mutation transfers to the plasmid by recombination with the chromosomal galTN102 cistron. Plasmid pI24 galTN102 was then introduced into a $Gal^+$ derivative of N6345 that arose as a result of Ref action. To detect pI24 $gal^+$ plasmids, which arise by recombination with the chromosomal $gal^+$ allele, applicants extracted plasmid DNA and transformed a gal mutant host. $Gal^+$ transformants were selected, and the structure of the pI24 $gal^+$ plasmid was analyzed by digestion with restriction endonuclease PstI. PstI incises pI24 once, in bla, whereas pI24 galTN102 is cut twice. The $gal^+$ recombinant plasmid was cut once, to yield a linear molecule identical in size to pI24 (data not shown).

Expression of Ref. N6405 carrying pLSD13 or control plasmids were grown in Luria broth plus 50 μg of ampicillin per ml at 32° C. to a cell density of ca. $10^8$/ml and then shifted to 42° C. for various times. Culture samples (1 ml) were then centrifuged, and the cell pellets were washed once with 200 μl of 10% trichloroacetic acid and twice with 300 μl of acetone. After being dried, the samples were suspended in 100 μl of loading buffer and heated for 5 to 10 min at 95° to 100° C. After centrifugation, 30-μl supernatant samples were added to a sodium dodecyl sulfate-polyacrylamide gel (15% polyacrylamide). After electrophoretic separation of the proteins, the gels were stained with Coomassie blue stain.

RESULTS

P1c1.100 stimulates precise excision of an IS1 transposon. E. coli K-12 strain N6345 bears the mutation galTN102, consisting of an IS1 insertion in galT. IS1 is bracketed by a 9-bp duplication (CGCCGCTAC) of galT sequence (Grindley, N. D. F. 1978. Cell 13:419–426). $Gal^+$ revertants of N6345 appeared at low frequency, presumably arising as the result of recombination between the duplicated sequences. This precise excision is largely independent of the host recA recombination pathway.

To measure the frequency of precise excision, applicants followed the appearance of $Gal^+$ (red) papillae within $Gal^-$ (white) colonies on MacConkey galactose indicator plates (Table 1). After overnight incubation at 32° C., N6345 yielded approximately 1 $Gal^+$ papilla per $10^5$ colonies. N6345 lysogenic for P1 reverted to $Gal^+$ at the same frequency. However, N6345 lysogenic for P1c1.100 yielded at least 1 $Gal^+$ papilla per colony. The function expressed by the P1c1.100 prophage that stimulates precise excision is identical to Ref, which promotes microhomologous recombination in lacZ (Windle, B. E. and J. B. Hays. 1986. Proc. Natl. Acad. Sci. USA 83:3885–3889). It is most likely that ref expression is inhibited by the P1 c1 product and that the P1c1.100 mutant repressor is partially defective at 32° C. N6345 lysogenic for phage P7, a p1-related phage which carries the same c1 gene as P1, showed no increase in precise excision of the IS1 element (Table 1).

TABLE 1

| Stimulation of IS1 precise excision by prophage P1 | |
|---|---|
| Prophage[a] | Efficiency of Precise Excision[b] |
| None | $1 \times 10^{-5}$ |
| P1c11.100 | 1 |
| P1 | $1 \times 10^{-5}$ |
| P7 | $1 \times 10^{-5}$ |
| λLD101 | 1 |
| λLD102 | 1 |

[a]Both P1 and P1c1.100 carried a chloramphenicol resistance marker, and P7 carried an ampicillin resistance marker; lysogens were selected by the appropriate antibiotic resistance.
[b]The efficiency of precise excision of the galTN102 IS1 insert carried in strain N6345 was determined as follows. N6345 and its derivatives were purified on MacConkey galactose plates at 32° C. White ($Gal^-$) colonies were inoculated into Luria broth and grown overnight at 32° C. with aeration. Cultures were diluted, spread on MacConkey galactose plates, and incubated 72 h at 32° C. An efficiency of $1 \times 10^{-5}$ indicates that only one colony in $10^5$ displayed a $Gal^+$ papilla; an efficiency of 1 indicates that every colony showed at least one $Gal^+$ papilla.

To demonstrate that Ref stimulates recombination between the duplication flanking the Is1 element, applicants analyzed gal DNA from a $Gal^+$ revertant of an N6345 (P1c1.100) lysogen. This involved several recombinational steps to cross the chromosomal gal DNA onto a plasmid (see Materials and Methods). The size of the $gal^+$ plasmid and its restriction pattern were consistent with the hypothesis that Ref stimulates the precise excision of the IS1 element, reverting the galTN102 mutation.

Subcloning the P1 ref gene into λD69. Applicants isolated a λ clone carrying the P1 ref gene, using a screen for Ref activity. N6345 infected with a λ ref clone is expected to yield numerous $Gal^+$ survivors. On MacConkey galactose plates seeded with N6345, λ ref plaques will contain red papillae.

To clone ref, applicants digested P1 DNA with BamHI and ligated the fragments with BamHI-digested λD69. The λD69 vector accepts compatible DNA fragments into a single BamHI site in the lambda int gene; recombinant clones are detected by a plate test for Int function (Mizusawa, S. and D. F. Ward. 1982. Gene 20:317–322). Applicants then tested 80 Int⁻ recombinant clones for Ref activity as described above. Two recombinant clones gave red plaques on lawns of the tester strain and were further analyzed.

DNA from the two Ref⁺ λD69 clones, λLD101 and λLD102, was isolated and subjected to restriction enzyme analysis. Both phage clones carry the same ca. 1.8-kb P1 DNA fragment. The sensitivity of the fragment to EcoRI indicates that ref is encoded by the BamHI-8 fragment of P1 (Yarmolinsky, M. B. and N. Sternberg. 1988. Bacteriophage P1. In R. Calender (ed.), The Bacteriophages. Plenum Publishing Corp., New York); the EcoRI restriction pattern also demonstrated that the BamHI-8 fragment was carried in different orientations in λLD101 and λLD102 (data not shown). Since both phages are phenotypically Ref⁺, applicants believe that the cloned fragment carries the ref promoter(s). This hypothesis is supported by the behavior of N6345 lysogens bearing λLD101 or λLD102 as prophages. Both strains show the same elevated frequency of precise excision as that of a N6345(P1c1.100) lysogen (Table 1). Furthermore, the Ref activity of both λ prophages was inhibited by wild-type P1 or P7 (Table 2). This is consistent with the idea that the ref promoter is negatively regulated by a P1 gene product.

TABLE 2

Inhibition of Ref by P1 and P7[a]

| Prophage 1 | Prophage 2 | Efficiency of Precise Excision |
| --- | --- | --- |
| λLD101 | None | 1 |
| λLD102 | None | 1 |
| λLD101 | P1 | $1 \times 10^{-5}$ |
| λLD101 | P7 | $1 \times 10^{-5}$ |
| λLD102 | P1 | $1 \times 10^{-5}$ |
| λLD102 | P7 | $1 \times 10^{-5}$ |

[a]Construction of lysogens is described in Results. The calculation of efficiency of precise excision is as in footnote b of Table 1.

Effect of host mutations on Ref activity. Applicants next tested the effect of various host mutations on the precise excision of IS1 from galT. As predicted from previous data showing transposon excision to be independent of the RecA pathway (Lundblad, V. and N. Kleckner. 1985. Genetics 109:3–19), Gal⁺ papillation in N6345, although reduced in frequency, was not eliminated in recA hosts. Mutations inactivating the general recombination gene recB or the himA gene, which is required for certain site-specific recombination events (1a) did not affect the rate of IS1 excision (data not shown). Mutant strains lysogenic for P1c1.100 or for λLD101 were constructed, and their rate of papillation was measured. In recB and himA mutants, Ref stimulation of precise excision was not significantly reduced (data not shown). However, neither P1c1.100 nor λLD101 increased the frequency of Gal⁺ papillation in recA cells. Thus, the stimulation by Ref of IS1 excision was entirely dependent on RecA. The requirement for RecA appears to be direct, rather than through RecA induction of the SOS pathway. Ref activity was not reduced by the lexA3 mutation. The lexA3 protein is resistant to RecA proteolytic cleavage; lexA3 mutants, therefore, do not undergo SOS induction. Applicants cannot determine whether Ref stimulates that proportion of the excision reaction which is RecA dependent or whether it acts through a recombination pathway not normally utilized for transposon excision.

Identification and sequence of the P1 ref gene. The structure of the ref gene was determined by a series of subclonings from λLD101 (FIG. 1). First, applicants subcloned the P1 BamHI-8 fragment into the BamHI site of pBR322. The resultant plasmid (pLD3) could only be isolated in a P1 lysogen. This suggested the presence in the cloned fragment of a P1-repressible function capable, at high copy number, of killing a nonimmune host cell. Further genetic manipulations of pLD3 indicated that this putative P1 function, kil, was distinct from ref. Deletion of pLD3 from the PvuII to the HpaI sites yielded the Ref⁺ Kil⁺ plasmid pLSD1. Deletion of pLSD1 DNA between the EcoRI site in the P1 fragment and the pBR322 EcoRI site yielded the Ref⁻ Kil⁺ plasmid pLSD4, whereas a P1 DNA BamHI-HincII fragment (in pLSD10) is Ref⁺ Kil⁻. Applicants conclude that ref lies between the HincII and BamHI sites.

Figure 3:
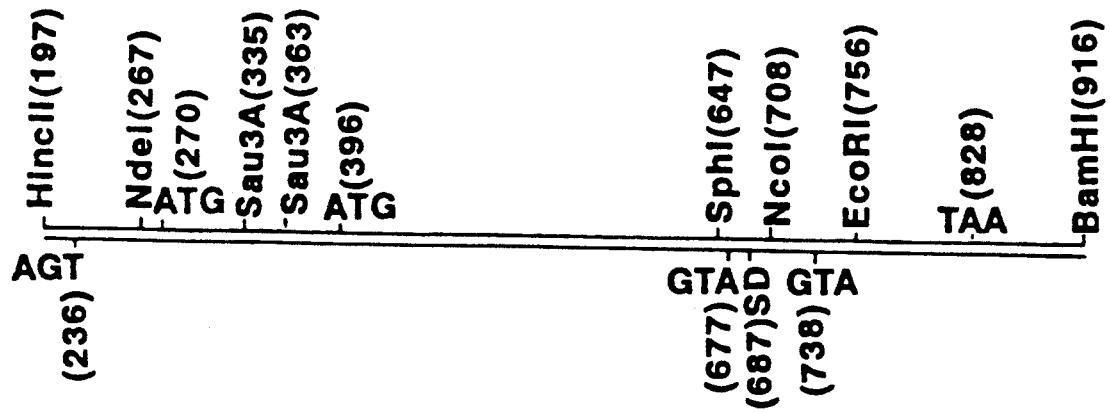
FIG. 3. Open reading frames on the HincII-BamHI P1 DNA fragment. The locations of the larger open reading frames relative to various restriction enzyme sites are shown. A potential ribosome-binding site is indicated (SD at coordinate 687). The ref gene is located between coordinates 270 and 830.

The 720-bp BamHI-HincII fragment was sequenced on both strands, using the Sanger dideoxy sequencing strategy (Sanger, F., et al. 1977. Proc. Natl. Acad. Sci. USA 74:5463–5467). The sequence of the strand encoding ref and the predicted amino acid sequence of Ref is shown in FIG. 2. Although the BamHI-HincII fragment carries open reading frames on both strands (FIG. 3), applicants were able to assign ref to the top strand on the basis of restriction enzyme analysis. As previously mentioned, deletion of DNA between EcoRI and BamHI (coordinates 756 to 916) yielded the Ref⁻ plasmid pLSD4. Similarly, a derivative of pLSD1 was digested with NcoI (coordinate 708) or SphI (coordinate 674) and religated after removal of the cohesive ends by S1 nuclease digestion. The resultant plasmids displayed no Ref activity. Cleavage with NdeI and removal of nucleotides between coordinates 197 and 270 yielded the Ref⁺ plasmid pLSD13 (see below). These considerations indicate that ref is encoded by a top-strand open reading frame and is transcribed in the same direction as the upstream cre gene (Yarmolinsky, M. B. and N. Sternberg. 1988. Bacteriophage P1. In R. Calender (ed.), The Bacteriophages. Plenum Publishing Corp., New York). Note that the top-strand open reading frame does not carry a canonical ribosomal-binding site and that there are two in-frame AUG initiation codons. Cleavage of pLSD1 with Sau3A (coordinate 363) yielded a fragment carrying the second, but not the first, ATG. When this 553-bp fragment was placed in BamHI-treated pBR322, applicants obtained pLSD16, which showed weak Ref⁺ activity FIG. 1). In pLSD16, the Sau3A fragment was transcribed from the ptet promoter of the plasmid. A plasmid carrying the fragment in the reverse orientation, pLSD17, displayed no Ref activity. This result suggests that the appropriate start of the ref gene is the upstream AUG and that the carboxy-terminal Ref fragment initiating at the second AUG (coordinate 396) is partially active. Other explanations for the weak Ref⁺ phenotype of the Sau3A fragment are not, however, ruled out.

With the aim of overproducing Ref, applicants cloned the ref gene into the λ $p_L$ expression vector, pKC30, and its derivative, pOG7 (Oppenheim, A. B., et al. 1982. J. Mol. Biol. 158:327–346; Rao, R. N. 1984.

Gene 31:247-250). To prevent cell death due to $p_L$ activity, all plasmids carrying the λ $p_L$ promoter were maintained in λ lysogenic strains. To test for Ref activity, the plasmids were introduced into N6345 lysogenic for λ cI+. Strain N6405, which carries a partially deleted λ cI857 N+ prophage, was used as a host when overproduction of Ref was desired. Subcloning of ref from pLSD1 into pKC30 yielded the Ref+ plasmid pLSD10 (FIG. 1). To activate λ $p_L$, a culture of N6405(pLSD10) was shifted from 32° C. to 42° C. Although thermal induction led to cell death, as a result of λ $p_L$ promoter activity, applicants could not detect Ref protein on sodium dodecyl sulfate-polyacrylamide gels (data not shown). Applicants assumed that the failure to find Ref reflected the absence of a ref ribosome-binding site. To obtain efficient translation of ref, applicants fused it with the λ cII gene. Plasmid pLSD10 was digested with NdeI, which cleaves at the putative ATG initiation codon of ref, and the ref fragment was inserted into a λ cII plasmid, pOG7, which had been cut with NdeI at the ATG initiation codon of cII. These manipulations yielded pLSD14, which carries ref in the antisense orientation relative to λ $p_L$. Digestion of pLSD14 with NdeI, followed by ligation, then yielded the appropriate plasmid, pLSD13, which carries a $p_L$-cII-ref fusion; the ref ATG is preceded by the canonical ribosome-binding site of λ cII. Both pLSD14 and pLSD13 were Ref+ but that the latter showed more activity than the other ref plasmids described above (FIG. 1).

Figure 4:
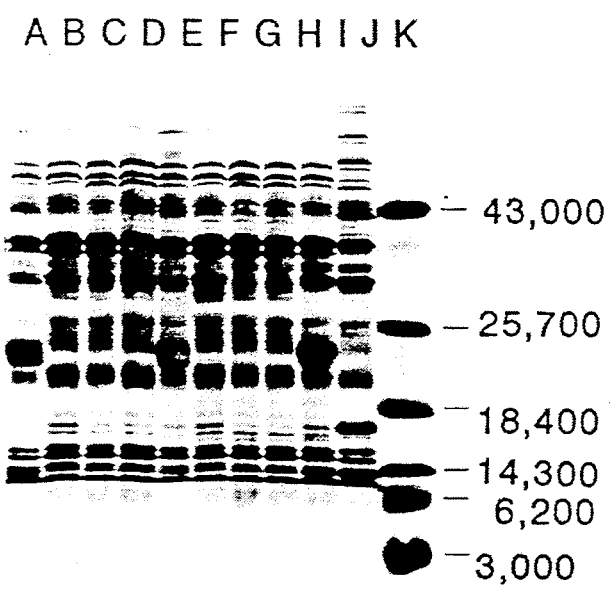
FIG. 4. Ref protein synthesis after thermal induction of $\lambda$ $p_L$ plasmids present in a $\lambda$ cI857 lysogen (N6405) is shown. In pLSD13, ref is preceded by the ribosome-binding site of the $\lambda$ cII gene and is transcribed from $p_L$. pLSD15 is pLSD13 ref::Tn10. Transcription of pLSD14 from $p_L$ is antisense. Proteins were extracted, separated electrophoretically on sodium dodecyl sulfate-polyacrylamide gels, and stained with Coomassie blue. Lanes A, E, and I, N6405(pLSD13) at 2, 3, and 4 h after induction, respectively; lanes B, F, and J, induction of pLSD15 at the same time points; lanes C and G and lanes D and H, pLSD14 and vector plasmid pKC30, respectively, at 3 (C and D) and 4 (G and H) h after induction. Positions (in kilodaltons) of molecular mass markers are shown to the right of the gel.

A time course of induction for the $p_L$-ref expression vectors is shown in FIG. 4, which displays, by Coomassie blue staining, the protein content of N6405(pLSD13) at 2, 3, and 4 h after a shift to 42° C. Induction of the λ cI857 lysogen carrying plasmid pLSD13 (FIG. 4, lanes A, E, and I) (strain N7298 (ATCC Accession No. 68326) is strain N6405 carrying the overproducing plasmid) resulted in the extensive synthesis of a protein of approximately 23 kilodaltons (kDa); the predicted $M_w$ of Ref is 22.8 kDa. Strains carrying control plasmids pLSD14 or pKC30 did not accumulate this protein (lanes C and G and lanes D and H, respectively). No protein of this molecular weight was observed in strains carrying pLSD13 before induction (data not shown).

Inactivation of ref by Tn10 insertion. To determine the role of Ref in P1 physiology, applicants isolated a P1 ref mutant phage, in which ref was inactivated by a mini-Tn10 insertion. Applicants first constructed an integration-proficient λ ref clone in which the P1 BAM-8 fragment was inserted at the BamHI site at nucleotide 41732 in a derivative of λ imm[21]. This phage (BMG200) was then grown lytically on a strain bearing plasmid pNK1340, which carries a readily transposable 2.9-kb mini-Tn10 element. Phage scoring as Ref− were detected on MacConkey galactose agar plates as white-plaque formers on N6345; the presence of the Tn10 element in ref was verified by restriction analysis of the phage DNA (data not shown). A strain containing the λref::Tn10 and plasmid pLSD13 was then constructed, and plasmid DNA was isolated. pLSD13 ref::Tn10 recombinants (pLSD15) were isolated by transforming N6405 and selecting for tetracycline resistance. The pattern of protein synthesis seen after induction of N6405(pLSD15) is shown in FIG. 4. Note the gradual appearance of a protein of approximately 16 kDa (FIG. 4, lanes B, F, and J). This size is consistent with a truncated amino-terminal fragment of Ref. To transfer the ref::Tn10 mutation from the plasmid into phage P1, P1c1.100 or P1c1.100cream was grown lytically on N6405(pLSD15). The lysates were mixed with N6345 and P1 ref::Tn10 lysogens were isolated as tetracycline-resistant colonies. The presence of the mini-Tn10 within the P1 virion DNA was shown by restriction analysis and the absence of Ref function was shown by measuring the rate of Gal+ papillation (data not shown). The mini-Tn10 is located approximately 310 bp from the amino-terminal end of ref.

Comparisons of the P1 ref mutants with wild-type P1 did not reveal significant defects in lytic growth after infection or induction (data not shown). The efficiency of lysogenization was likewise not dramatically affected by the ref mutation, although in certain experiments, P1 ref mutants showed two- to fivefold-lower frequencies of lysogenization. The cause of this variability has not been determined. In recA cells, lysogenization efficiency was poor and was, as previously reported, dependent upon Crepromoted circularization of P1 chromosomes carrying redundant lox sites (Sternberg, N., et al. 1986. J. Mol. Biol. 187:197-212). These results confirm the report by Windle and Hays (Windle, B. E. and J. B. Hays. 1986. Proc. Natl. Acad. Sci. USA 83:3885-3889), who likewise failed to detect a consistent phenotype for a P1 ref mutant. Apparently, circularization of the P1 chromosome is not measurably influenced by Ref recombination.

DISCUSSION

Applicants have demonstrated the presence in phage P1 of a gene, ref, whose product stimulates the precise excision of an IS1 element inserted within the *E. coli* galT gene. The ref gene was independently detected and described by Windle and Hays (Windle, B. E. and J. B. Hays. 1986. Proc. Natl. Acad. Sci. USA 83:3885-3889; Windle, B. E., et al. 1988. J. Bacteriol. 170:4881-4889), who noted that P1 stimulated recombination within the *E. coli* lac operon. Enhancement of IS1 excision by Ref shows an absolute requirement for the RecA protein but is unaffected by recB (exonuclease V) or himA (integrative host factor) mutations. Windle and Hays (Windle, B. E. and J. B. Hays. 1986. Proc. Natl. Acad. Sci. USA 83:3885-3889) have previously reported that maximal enhancement of lacZ recombination by Ref requires a functional recBCD pathway.

The spectrum of insertional mutations acted upon by Ref has not been extensively explored. However, a lacZ::Tn10 mutation is reported to be refractory to Ref-stimulated precise excision (Windle, B. E. and J. B. Hays. 1986. Proc. Natl. Acad. Sci. USA 83:3885-3889). Furthermore, P1 transduction of the GalTN102 mutation into C600 yielded both Ref-sensitive and Ref-resistant colonies (S.D.L., D.L., and M.G., unpublished observations). The reason for this apparent specificity is not known.

Ref activity was detected in lysogens bearing P1c1.100; cells lysogenic for wild-type P1 showed no increase in precise excision. Ref may actually be a P1 lytic function, normally repressed in wild-type P1 lysogens but expressed in cells carrying the partially defective c1.100 repressor. P1 cI product is, however, not sufficient for repression of ref (S.D.L., D.L. and M.G., unpublished observations); P1 bof product must also be present (Windle, B. E., et al. 1988. J. Bacteriol. 170:4881-4889).

Applicants have cloned and sequenced the ref gene. It encodes a protein of 22.8 kDa and is located close to another P1 recombination function, cre. A P1 function lethal to E. coli, kil, lies between the two genes. The absence of a canonical ribosome-binding site suggests that ref is not abundantly expressed in P1. In fact, applicants failed to detect Ref protein after induction of pBR322 constructs carrying ref downstream to the efficient λ $p_L$ promoter. To visualize ref product on Coomassie blue-stained gels, it was necessary to fuse the λ cII ribosome-binding site to the ref initiation codon.

Ref is a relatively basic protein (37 basic and 20 acidic amino acids). It bears little resemblance to other phage proteins active in recombination (Argus, P., et al. EMBO J. 5:433-440; A. Landy, personal communication). Preliminary experiments suggest that Ref binds to DNA; applicants have thus far been unable to demonstrate any specificity in this reaction. Applicants, and Windle and Hays (Windle, B. E. and J. B. Hays. 1986. Proc. Natl. Acad. Sci. USA 83:3885-3889), isolated P1 ref null mutants. These mutants displayed no significant changes in their lytic pathway and only small and variable reductions in lysogenic efficiency. Therefore, under the conditions in which P1 physiology is studied, Ref can play only an auxiliary role. It might stimulate circularization of the P1 chromosome in the presence of RecA; if so, this stimulation is not detectable as a significant increase in P1 burst size or lysogenization efficiency. Ref stimulates recombination between widely spaced lacZ markers four- to fivefold, suggesting that Ref might stimulate recombination in general, and not only recombination between small homologous sequences (J. Hays, personal communication). It will be interesting to determine whether Ref affects recombination between P1 genes.

How Ref stimulates microhomologous recombination remains to be elucidated. One model proposes that Ref reduces the threshold for homology required for RecA activity; RecA does not pair DNA molecules with 30 bp or less homology (Gonda, D. K. and C. M. Radding. 1983. Cell 34:647-654). Certainly, the 9-bp duplication generated by IS1 insertion is too small to serve as a substrate for RecA-promoted recombination. Ref may enhance RecA-dependent pairing reactions between minimally homologous DNA molecules.

What is claimed is:

1. An expression plasmid designated pLSD13.

2. An *Escherichia coli* 7298 cell (ATCC Accession No. 68326) comprising the pLSD13 expression plasmid of claim 1.

3. A method of producing a purified protein having a molecular weight of about 22.8 kD, the amino acid sequence shown in FIG. 2 and the ability to ligate double-stranded DNA molecules, which comprises culturing the *Escherichia coli* 7298 cell of claim 2 under conditions such that the pLSD13 plasmid contained therein expresses the protein and then recovering the protein so expressed.

* * * * *